United States Patent [19]

Sih

[11] 4,444,884

[45] Apr. 24, 1984

[54] PROCESS FOR PREPARING STEROIDS

[75] Inventor: Charles J. Sih, Madison, Wis.

[73] Assignee: Wisconsin Alumni Research Foundation, Madison, Wis.

[21] Appl. No.: 420,982

[22] Filed: Sep. 21, 1982

Related U.S. Application Data

[63] Continuation-in-part of Ser. No. 382,011, May 25, 1982, abandoned.

[51] Int. Cl.³ .......................... C12P 33/16; C12N 1/38
[52] U.S. Cl. ........................................ 435/55; 435/244
[58] Field of Search .................................. 435/55, 244

[56] References Cited

U.S. PATENT DOCUMENTS

| | | | |
|---|---|---|---|
| 3,684,657 | 8/1972 | Kraychy et al. | 435/55 |
| 3,759,791 | 9/1973 | Marsheck et al. | 435/55 |
| 3,943,038 | 3/1976 | Morinaga et al. | 435/244 |
| 4,035,236 | 7/1977 | Wovcha | 435/55 |
| 4,179,336 | 12/1979 | Weber et al. | 435/55 |

*Primary Examiner*—Alvin E. Tanenholtz
*Attorney, Agent, or Firm*—Howard W. Bremer

[57] ABSTRACT

The invention provides a method for enhancing the degradation of the side chain of sterols possessing branched chains at C-24 utilizing microbiological means by including an exogenous source of bicarbonate ion ($HCO_3^-$) in the medium in which the degradation is being carried out.

12 Claims, No Drawings

PROCESS FOR PREPARING STEROIDS

The invention described herein was made in the course of work under a grant or award from the Department of Health and Human Services.

This application is a continuation-in-part of application Ser. No. 382,011, filed May 25, 1982, abandoned.

TECHNICAL FIELD

This invention relates to steroid hormones and more particularly to microbiological processes for converting readily available sterols into useful intermediates for the synthesis of more difficultly obtainable steroid hormones. Still more particularly this invention relates to processes for selectively degrading naturally occurring sterols at the C-17 position without concomitant ring cleavage, to obtain intermediates useful in synthesizing steroid hormones.

Background Art

Utilization of the soybean sterols, sitosterol, campesterol and stigmasterol as an economic source of intermediates for steroid manufacture has been long considered for supplementing or supplanting the commercial processes from diosgenin, obtained from the Barbasco root and other sources (R. Wiechert, *Angew. Chem. Int. Ed. Engl.*, 9, 321, 1970). Several microbiological processes are now available for the conversion of phytosterols or modified phytosterols (19-oxygenated) into useful androstane steroids. (See for example C. K. A. Martin, *Adv. in Applied Microbiol.*, 22, 28, 1977).

Disclosure of Invention

Broadly the present invention comprises the enhancement of the efficiencies of the cleavage of sterols possessing branched chains at C-24. It has been found that this can be accomplished by the addition of bicarbonate ions to the fermentation medium. More specifically, it has now been found that the efficiencies of the microbiological degradation of the side chains of sitosterol and campesterol, stigmasterol or their modified derivatives are greatly improved if an exogenous source of $HCO_3^-$ ion is included in the medium. Examples of microorganisms which respond to $HCO_3^-$ ion during the cleavage of the phytosterol side chain are those of the genera Nocardia, Mycobacterium, Arthrobacter and Corynebacterium. (See for example, U.S. Pat. No. 3,507,749.)

Although there is no intention to be bound by the following threoretical considerations, it is believed that in the fermentation the microorganisms function to degrade the steroid compound initially by oxidation at the C-26 position, introduction of unsaturation at C-24-C-25, incorporation of $HCO_3^-$ at C-28 before any carbon-carbon breakage of the hydrocarbon side chain takes place. After hydration at C-24, the phytosterol side chain of the sitosterol class is converted into 3-oxo-chol-4-en-24-oic acid and two moles of propionic acid. In the case of campesterol, it is converted into 3-oxo-chol-4-en-24-oic acid accompanied by one mole of acetic acid and one mole of propionic acid. The further transformation of 3-oxo-chol-4-en-24-oic acid into 17-keto steroids are well known. (C. J. Sih et al., *Biochemistry*, 7, 808, 1968.)

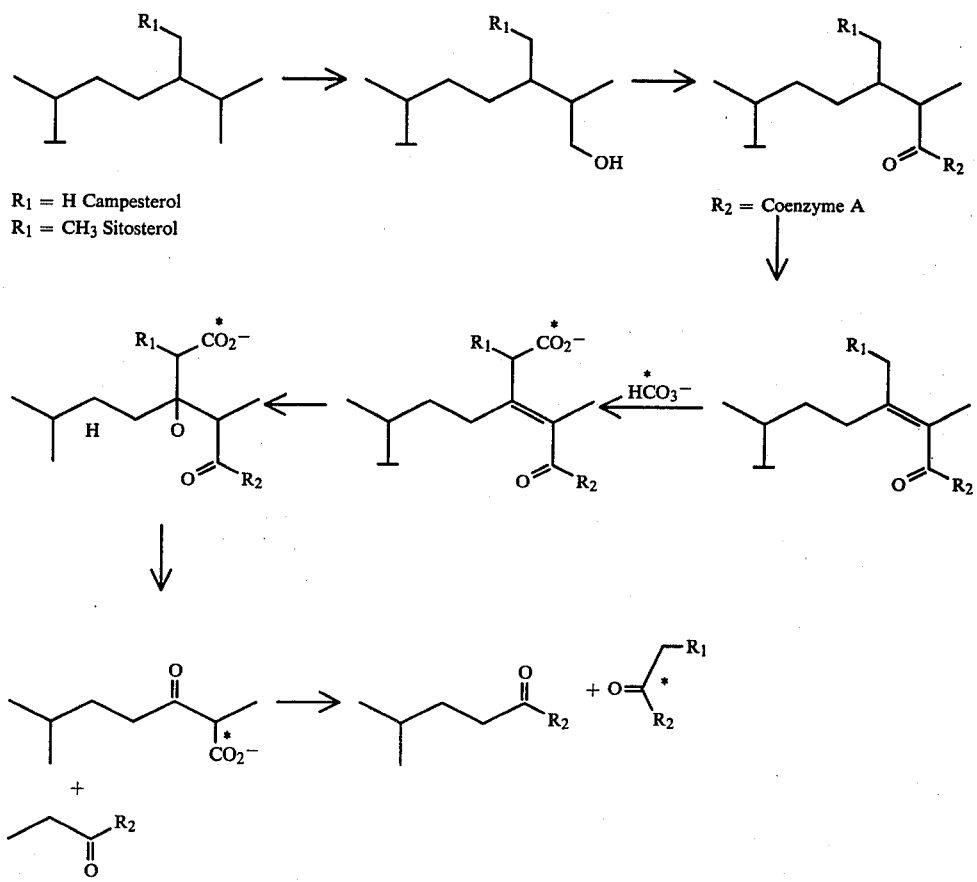

$R_1$ = H Campesterol
$R_1$ = $CH_3$ Sitosterol $R_2$ = Coenzyme A

The above scheme merely emphasizes the need of bicarbonate ion during the degradation. The concentrations of bicarbonate ion present in a normal medium is insufficient for this process to operate at maximum efficiency especially when high concentrations of phytosterols or their derivatives are present. For the degradation to operate at maximum efficiency an exogenous source of $HCO_3^-$ ion must be supplied. This can be supplied in many forms such as $NaHCO_3$, $NH_4HCO_3$, $CaCO_3$, $CO_2$, $H_2CO_3$, i.e. a one carbon unit chemical compound which can be converted by the microorganism (the enzymes elaborated by the microorganisms) to the bicarbonate ion or $CO_2$. It should be emphasized that the form in which the $HCO_3^-$ supplied is not critical or limiting as long as the form in solution required by the microorganism for incorporation into the C-24 position is an activated form of bicarbonate ion (e.g., bicarbonate bound to coenzyme). One of the most effective means for supplying the ion has been found to be the simple expedient of introducing (as by bubbling) $CO_2$ through the fermentation medium while fermentation is progressing.

Microorganisms which are characterized by their ability to degrade the side chain of phytosterols are well known in the art (see Martin, *Adv. in Appl. Microbiol.*, 22, 28, 1977 and U.S. Pat. No. 3,507,749). Any of the genera of microorganisms described therein can be employed in the process of this invention. The sterol starting material can be incorporated in a nutrient medium of standard composition in which such organisms are cultivated and the usual conditions of fermentation can then be employed to effect the sterol conversion. Alternatively, the active principle can be removed from the growing culture of microorganisms, for instance, by lysis of the cells to release the enzymes, or by suspension of the cells in a fresh aqueous system, or by immobilization of cells. In any of these techniques the 17-side chain of the sterol will be selectively cleaved, so long as the active principle elaborated by the microorganism is present in the medium. Of course, the temperature, time and pressure conditions under which the contact of the phytosterol derivative with the degradative principle is carried out are interdependent as will be apparent to those skilled in this art. For instance, with gentle heating and at atmospheric pressure the time required to effect the sterol conversion will be less than at room temperature under conditions otherwise the same. Of course, neither temperature nor pressure nor time should be so great that the sterol is thereby degraded. Where a growing culture of the organism is used, the process conditions should also be sufficiently gentle so the organism is not killed prematurely, i.e. before it elaborate sufficient enzymes. Generally speaking, the temperature can range from about 10° C. to about 37° C. and the time from about 12 hours to about 12 days.

BEST MODE FOR CARRYING OUT THE INVENTION

The following examples are given to illustrate this invention but are not to be construed in any way to limit its scope.

EXAMPLE I (A) Fermentation—Surface growth from a one week old agar slant of Mycobacterium sp. NRRL B-3805 grown on agar of the following composition:

| Glucose-Agar Solid Medium | Gms |
| --- | --- |
| Agar | 20 |
| Glucose | 10 |
| Yeast extract | 2.5 |
| $K_2HPO_4$ | 1 |
| Distilled water, q.s. 1 liter | |
| (Sterilized 15 minutes at 20 p.s.i.) | | was suspended in 5 ml of an 0.85% saline solution. One ml portions of this suspension were used to inoculate a 250 ml Erlenmeyer flask (F-1 stage) each containing 60 ml of the soybean-dextrose medium (SDM):

| Soybean Dextrose Medium (SDM) | Gms |
| --- | --- |
| Soybean meal | 5 |
| Dextrose | 20 |
| Yeast extract | 5 |
| $K_2HPO_4.7H_2O$ | 8.7 |
| Sitosterol (containing campesterol) | 0.1 |
| Tap water, q.s. 1 liter, adjusted to pH 7.8 | |
| (Sterilized 20 min at 30 p.s.i.) | |

The flasks were incubated at 25° C. on a rotary shaker (200 cycles/min—2" radius) for 48 hours, after which a 10% by volume transfer was made to a series of 250 ml Erlenmeyer flasks (F-2 stage) each containing 60 ml of the above medium. After 48 hours, 120 mg of sitosterol, suspended in 5 ml of 1% Tween 80, was added to each flask resulting in a final substrate concentration of 2 mg/ml. At the same time various amounts of $NaHCO_3$ powder was added to each flask to give the indicated $HCO_3^-$ concentrations. The flasks were incubated under the same conditions as the F-1 stage flasks. The pH was maintained at 7.6±0.1 by the addition of sterile $1M$ $KH_2PO_4$ solution each day.

(B) Quantative analysis of androst-4-ene-3,17-dione—Forty-eight hours after the addition of the sitosterol, each flask was extracted separately with ethyl acetate (50×3). The combined extracts were washed with water, dried over $Na_2SO_4$, and evaporated to dryness in vacuo. A portion of the residue was dissolved in acetone and chromatographed over a 10×20 cm thin-layer plate [EM—0.5 mm thickness silica gel containing PF254 indicator, Brinkmann] and developed in a system which consisted of: ethyl acetate-hexane (1:1). Sitosterol has $R_f=0.49$; androst-4-ene-3,17-dione has $R_f=0.27$. The UV absorbing band corresponding to androst-4-ene-3,17-dione was eluted exhaustively with ethyl acetate and the UV absorbancy at 240 nm ( =15,000) was measured. The results were as follows:

| Concentration of $HCO_3^-$ (mM) | m moles of androst-4-ene-3,17-dione |
| --- | --- |
| 0 | 55.7 |
| 25 | 99.0 |
| 50 | 91.1 |
| 75 | 94.2 |

EXAMPLE 2

(A) Fermentation—Surface growth from a one-week old agar slant of Mycobacterium sp. NRRL-3683, grown on the glucose-agar solid medium, was suspended in 5 ml of an 0.85% saline solution. One ml portions of this suspension were used to inoculate a 250 ml Erlenmeyer flask (F-1 stage) each containing 60 ml of the soybean-dextrose medium (SDM). The flasks were incubated at 25° C. on a rotary shaker (200 cycles/min—2" radius) for 48 hours, after which a 10% by volume transfer was made to a series of 250 ml Erlenmeyer flasks (F-2 stage) each containing 60 ml of the SDM medium. After 48 hours of incubation (same as F-1 stage), 120 mg of sitosterol (containing campestero), suspended in 5 ml of 1% Tween 80 was added to each flask. At the same time various quantities of $NaHCO_3$ powder was added to each flask to give the desired $HCO_3-$ concentration. The flasks were incubated on the rotary shaker (same as F-1 stage) and at 48 and 116 hours, samples were analyzed for androsta-1,4-diene-3,17-dione.

(B) Quantitative analysis of androsta-1,4-diene-3,17-dione (ADD). At the indicated time intervals (48 hrs and 116 hrs), each flask was adjusted to pH 3 and extracted separately with ethyl acetate (50 ml×3). The combined extracts were washed with water, dried over $Na_2SO_4$, and evaporated to dryness in vacuo. A portion of the residue was dissolved in acetone and chromatographed over a 10×20 cm thin layer plate [EM—0.5 thickness silica gel containing PF254 indicator, Brinkmann] and developed in a system consisting of ethyl acetate-hexane (1:1). Sitosterol has $R_f=0.49$; androsta-1,4-diene-3,17-dione (ADD) has $R_f=0.16$. The UV absorbing band corresponding to androsta-1,4-diene-3,17-dione was eluted exhaustively with ethyl acetate and the UV absorbancy at 244 nm ($\epsilon=15,000$) was measured. The results were as follows:

| | m moles of ADD | |
|---|---|---|
| $HCO_3-$ (mM) | 48 hrs | 116 hrs |
| 0 | 39.4 | 78.6 |
| 25 | 56.0 | 105.8 |
| 50 | — | 142.1 |
| 75 | 51.6 | 102.8 |
| 100 | 59.7 | 100.9 |

EXAMPLE 3

(A) Fermentation. Surface from a one-week old agar slant of *Mycobacterium phlei* NRRL-B-15050, grown on the glucose agar solid medium, was suspended in 5 ml of an 0.85% saline solution. One ml portions of this suspension were used to inoulate a 250 ml Erlenmeyer flask (F-1 stage) each containing 60 ml of the following medium:

| Glycerol-Medium A | Gms |
|---|---|
| Nutrient broth (Difco) | 8 |
| Yeast extract | 1 |
| Glycerol | 5 |
| $K_2HPO_4.7H_2O$ | 8.7 |
| Sitosterol (containing campesterol) | 0.1 |
| Tap water, q.s. 1 liter, adjusted to pH 7.8 | |
| (Sterilized 20 min at 30 p.s.i.) | |

After 48 hours of incubation (same as F-1 stage), 120 mg of sitosterol (containing campesterol) suspended in 5 ml of 1% Tween 80 was added to each flask. At the same time various quantities of $NaHCO_3$ powder was added to each flask to give the desired $HCO_3-$ concentrations. The flasks were incubated on the rotary shaker (same as F-1 stage) and at 48 and 96 hours, samples were analyzed for androsta-1,4-diene-3,17-dione (ADD).

| | m moles of ADD | |
|---|---|---|
| $HCO_3-$ (mM) | 48 hrs | 96 hrs |
| 0 | 18.4 | 40.8 |
| 25 | 42.7 | 67.3 |
| 50 | 46.0 | 69.4 |
| 75 | 42.4 | 64.8 |

In the foregoing Examples bicarbonate ion concentrations as high as 200 mM can be used with comparable results, although the preferred range is from 25 mM to 150 mM. In any event, concentrations should be used which will enhance the efficiencies of the selective cleavage of the 17-side chains of sterols possessing branched chains at C-24 but which will not adversely affect such cleavage.

It is to be understood that any of the microorganisms of the genera Nocardia, Mycobacterium, Arthrobacter and Corynebacterium (U.S. Pat. No. 3,507,749) which respond to the $HCO_3-$ ion during cleavage of the phytosterol side chain can be readily substituted for those microorganisms specified in the foregoing specific Examples and that comparable production of the desired product androsta-1,4-diene-3,17-dione or androst-4-ene-3,17-dione will be obtained.

I claim:

1. An improved process for preparing useful androstane steroids from phytosterols characterized by the presence of branched chains at C-24, which comprises selectively cleaving the 17-side chains of said phytosterols by exposing them to fermentative action of enzymes elaborated by a microorganism of the genus Nocardia, Mycobacterium, Arthrobacter or Corynebacterium characterized by the ability to cleave the 17-side chain of phytosterols and to respond to the $HCO_3-$ ion during the cleavage process, in the presence of a one carbon unit chemical compound which can be converted by the microorganisms to the bicarbonate ion, or $CO_2$, sufficient in amount to enhance the cleavage of the 17-side chain of the phytosterols but insufficient to adversely affect the elaboration of enzymes by the microorganism and recovering the desired androstane steroids.

2. The process of claim 1 wherein the exposure to the enzymes elaborated by the microorganism is accomplished during cultivation of the microorganism in an aqueous nutrient medium under submerged aerobic conditions.

3. The process of claim 2 wherein the bicarbonate ion is supplied by the introduction of carbon dioxide into the medium during the cultivation.

4. The process of claim 2 wherein the process is carried out at a temperature in the range from about 10° C. to about 37° C. for a period of about 12 hours to about 12 days.

5. The process of claim 2 wherein the exogenous source of bicarbonate ion ($HCO_3-$) is sufficient to a bicarbonate ion concentration in the range from about 25 mM to about 200 mM.

6. The process of claim 1 wherein the exposure to the enzymes elaborated by the microorganism is accomplished in a nutrient medium in which said enzymes have been incorporated after they have been released from a growing culture of the microorganisms and recovered.

7. The process of claim 1 wherein the phytosterol is sitosterol.

8. The process of claim 1 wherein the phytosterol is campesterol.

9. The process of claim 1 wherein the microorganism is of the genus Mycobaterium.

10. The process of claim 9 wherein the Mycobacterium is Mycobacterium sp. NRRL B-3805.

11. The process of claim 9 wherein the Mycobacterium is Mycobacterium sp. NRRL-3683.

12. The process of claim 9 wherein the Mycobacterium is phlei NRRL B-15050.

* * * * *